United States Patent
Hariharan

(10) Patent No.: US 9,682,039 B2
(45) Date of Patent: Jun. 20, 2017

(54) CHEMICALLY STABLE AND OROMUCOSALLY ABSORBABLE GEL COMPOSITIONS OF A PHARMACEUTICAL ACTIVE AGENT IN A MULTI-CHAMBERED DELIVERY SYSTEM

(71) Applicant: MUCODEL PHARMA LLC, Greensboro, NC (US)

(72) Inventor: Madhu Hariharan, Greensboro, NC (US)

(73) Assignee: MUCODEL PHARMA LLC, Greensboro, NC (US)

(*) Notice: Subject to any disclaimer, the term of this patent is extended or adjusted under 35 U.S.C. 154(b) by 0 days.

(21) Appl. No.: 14/820,081

(22) Filed: Aug. 6, 2015

(65) Prior Publication Data

US 2016/0038406 A1 Feb. 11, 2016

Related U.S. Application Data

(60) Provisional application No. 62/034,496, filed on Aug. 7, 2014.

(51) Int. Cl.
| | | |
|---|---|---|
| A61M 5/19 | (2006.01) | |
| A61K 31/485 | (2006.01) | |
| A61K 9/00 | (2006.01) | |
| A61K 47/10 | (2017.01) | |
| A61K 9/06 | (2006.01) | |
| A61K 47/32 | (2006.01) | |
| A61K 47/38 | (2006.01) | |

(52) U.S. Cl.
CPC .............. *A61K 9/009* (2013.01); *A61K 9/006* (2013.01); *A61K 9/06* (2013.01); *A61K 31/485* (2013.01); *A61K 47/10* (2013.01); *A61K 47/32* (2013.01); *A61K 47/38* (2013.01); *A61M 5/19* (2013.01)

(58) Field of Classification Search
None
See application file for complete search history.

(56) References Cited

U.S. PATENT DOCUMENTS

| | | | | |
|---|---|---|---|---|
| 6,116,900 | A * | 9/2000 | Ostler | A61C 5/00 433/215 |
| 6,284,765 | B1 * | 9/2001 | Caffrey | A61K 9/0043 514/263.32 |
| 8,642,086 | B2 * | 2/2014 | Coady | A61K 31/78 424/486 |
| 2008/0103169 | A1 * | 5/2008 | Phillips | A61J 1/20 514/303 |
| 2009/0023766 | A1 * | 1/2009 | Clarke | A61K 9/006 514/284 |
| 2014/0005218 | A1 | 1/2014 | Myers et al. | |
| 2014/0008366 | A1 | 1/2014 | Genosar | |
| 2014/0088486 | A1 | 3/2014 | Uhland et al. | |

OTHER PUBLICATIONS

Vishwas (Vishwas R., et al., Effect of surfactants and pH on naltrexone (NTX) permeation across buccal mucosa, Int J Pharm. Jun. 15, 2011; 411(1-2): 92-97).*
International Search Report issued in connection with corresponding Internatioal Application No. PCT/US15/44033, dated Nov. 4, 2015.

* cited by examiner

*Primary Examiner* — H. Sarah Park
(74) *Attorney, Agent, or Firm* — Fitch, Even, Tabin & Flannery, LLP

(57) ABSTRACT

An oromucosally absorbable liquid composition for administration to a human patient comprises one liquid containing a pH-sensitive pharmaceutically active together with one or more optional suitable pharmaceutical excipients in a first compartment; and a second liquid at pH greater than 5 containing a buffer or alkaline components together with one or more optional suitable pharmaceutical excipients in a second distinct compartment; the first and second compartments maintaining separation of the first and second liquids during storage and allowing for mixing of the two liquids to form an oromucosally absorbable composition at the point of use.

29 Claims, 7 Drawing Sheets

CHEMICALLY STABLE AND OROMUCOSALLY ABSORBABLE GEL COMPOSITIONS OF A PHARMACEUTICAL ACTIVE AGENT IN A MULTI-CHAMBERED DELIVERY SYSTEM

This application claims the benefit under 35 U.S.C. §119 (e) of U.S. Provisional Application No. 62/034,496, filed Aug. 7, 2014, the entire disclosure of which is hereby incorporated by reference. The present invention relates to pharmaceutically active drugs in general, and to opioid antagonists in particular, and to improved buccal, gingival and sub-lingual absorption of opioid antagonists, including such absorption of naloxone hydrochloride formulations.

FIELD OF THE INVENTION

Background of the Present Invention

Naloxone hydrochloride is a specific and effective opioid antagonist which acts competitively at opioid receptors in the brain and has been found to have a wide variety of medical uses, for example, in reversing of the effects of therapeutic or overdose quantities of opioid narcotic drugs. Thus, intravenous, intramuscular or subcutaneous naloxone hydrochloride is used in diagnosis and treatment of opioid over dosage and is also administered post-operatively to reverse central nervous system depression resulting from the use of opioids during surgery.

Naloxone is also used for treatment of overdose of illicit opioid narcotics. The most common method of treatment is the use of an injectable naloxone product such as NAR-CAN™ (or the newer product EVZIO™) which are available in the United States. These injectable products are commonly used in emergency room settings, and are also sometimes carried by law enforcement officials to rapidly reverse opioid overdose. A nasally administered naloxone spray to deliver an emergency dose of naloxone is also available in some countries. In the USA, the injectable product is currently used along with Mucosal Atomization Device (MAD™). Injectable and nasal naloxone are effective but not adequately portable to be routinely and conveniently carried on one's person. Furthermore, training is required for the administration of these products which may limit their widespread availability and use.

Some narcotic antagonists can also be used to dissuade addictive behavior. U.S. Pat. Nos. 8,673,355 and 7,749,542 and 7,419,686 and 7,172,767 and 6,696,066 and 6,475,494 and 6,277,384 teach the combination of an opioid antagonist and an opioid agonist to discourage patients from diverting the product for illicit parenteral use. However, these patents provide no teaching as to the delivery of an opioid antagonist by itself. Other patents related to the field of the present invention include U.S. Pat. Nos. 8,652,515, 8,524,275, 8,017,148, 7,842,307, 7,718,192, 7,682,634, 7,332,182, 7,144,587, 6,627,635, and 8,475,832. These patents and their contents are incorporated into this specification by reference and as if they were fully set forth herein.

U.S. Pat. No. 8,475,832 teaches the combination of an agonist and antagonist and discusses the use of buffers to limit the absorption of Naloxone in the oral cavity using a buffer with a pH of 3-4. However, there is neither a mention of optimizing the absorption of an antagonist, nor mention of how to stabilize the antagonist during storage. U.S. Pat. No. 7,682,634 teaches the use of seal coatings to keep the agonist and the antagonist separated. But again, this art is directed to a combination of the agonist (opioid) and the antagonist (naloxone). These patents and their contents are incorporated by reference in this specification and as if they were fully set forth herein.

It is well known that the permeation of ionizable molecules follows the pH-partition theory as explained by Chen et al, A mechanistic analysis to characterize oromucosal permeation properties. Int. J. of Pharmaceutics 184 (1999) 63-72, using nicotine as a model substance. The pH-partition theory was proved from the observations that permeability, partition coefficient and diffusivity of nicotine, varied as a function of pH. The neutral nicotine species had a higher permeability than the ionized species due to its higher partition coefficient and diffusivity via the transcellular pathway.

Vishwas, Rai, Hock S. Tan, Bozena Michniak-Kohn, "Effects of Surfactants and pH on Naltrexone (NTX) Permeation Across Buccal Mucosa" Int. J. Pharm. Jun. 15, 2011; 411(1-2): pp 92-97 ("Vishwas et al.") teaches the benefits of maintaining a pH of 6.8 to 8.2 for improved absorption of Naltrexone. For example, Vishwas et al states: "[s]lightly increasing the pH of NTX (naltrexone) from 6.8 to pH 7.5 and pH 8.5 increased permeation by a factor of 1.6 and 4.4 respectively." Id. at page 8, Conclusions, Section 4, Sentence 5. Naltrexone is an antagonist with a structure much like Naloxone but has a better affinity for the κ-opioid binding site. Vishwas et al. further teach the use of a particular surfactant to increase the buccal absorption of Naltrexone: "It was found that permeation of NTX across reconstituted human buccal mucosa produced an enhancement of 7.7 with the use of Brij 58." Id. at page 8, Conclusions, Section 4, Sentence 2. However, Vishwas et al. make no mention or suggestion of combining a surfactant with a pH buffer nor do they mention the use of two compartments to separate the buffer from the antagonist during the storage of the product. Nor do they teach how to have a storage-stable antagonist with a pH greater than 5 at the point of use.

Naloxone hydrochloride injection is formulated at a pH of approximately 4 to ensure stability of naloxone over the life of the product. The pKa of Naloxone is reported to be around 7.9 for the protonated amine. Based upon pH partition theory it may be expected that if the un-protonated species has higher permeability through the oral mucosae, then maximal absorption could be expected at or around pH 7.9. However, sufficient absorption to elicit a therapeutic response could conceivably occur at pH greater than 5 and up to 12.

U.S. Pat. No. 6,110,926 teaches that aqueous solutions of Naloxone with buffers at pH 6.5 are subject to degradation and tests have shown that such solutions are in fact unstable, the naloxone content degrading over the course of a few days. This patent claims that the instability may explain the report by Loimar et al (The Lancet, May 5, 1990, pp. 1107-1108) that conjunctival naloxone does not provide a decision aid in determining opioid addiction. This patent and the Lancet paper, and their contents, are incorporated by reference into this specification as if fully set forth herein. It must also be noted that injectable naloxone is typically at a pH of 4 adjusted with hydrochloric acid presumably to avoid this instability.

Again using naltrexone as an example, according to Vishwas et al., a pH of 6.5 is in the target pH range for optimizing the bioavailability (absorption) of the antagonist. However, neither the patents referenced above, nor Vishwas et al., teach how to both optimize the absorption of the antagonist and also protect the antagonist from pH-induced oxidation or hydrolysis during storage.

A rescue drug like naloxone cannot be administered orally to an unconscious patient who is unable to swallow an oral medication. However, even if Naloxone or like antagonists are given orally using conventional methods, they are subject to first pass metabolism, and degradation and are consequently not available for blocking of the opioid receptors at the relevant receptor sites in the body. Smith K; Hopp M; Mundin G; Bond S; Bailey P; Woodward J; Bell D. Low Absolute Bioavailability of Oral Naloxone in Healthy Subjects, "Int. J. of Clinical Pharmacology and Therapeutics, 2012; 50 (5); pp 360-367" ("Smith et al.") and Manir A. Hussain; Bruce J. Aungst; Albert Kearney; Eli Shefter "Int. J. of Pharmaceutics, Vol. 36, Issues 2-3, May 1987, pp 127-130" ("Hussain et al.") teach low systemic bioavailability of naloxone and naltrexone due primarily to metabolization by the liver. Smith writes "The mean absolute bioavailability of naloxone from the orally administered PR tablets was very low, ranging from 0.9% for the 5 mg dose to 2% for 40, 80, and 120 mg doses based on AUCt." See Abstract Results, Sentence 1. Hussain writes "Both naloxone and naltrexone have been shown to be absorbed from the gastrointestinal tract. However, as a consequence of rapid clearance by the gut and/or liver, naloxone and naltrexone undergo extensive first-pass metabolism when given orally." See id., page 129, ¶2. The major metabolite is naloxone-3-glucuronide which is excreted in the urine. The foregoing references and their contents are incorporated into this patent application by reference and as if fully set forth herein.

Although the prior art has taught the use of buffers and permeation enhancers to increase the buccal absorption of an antagonist, no one has taught how to deliver a shelf life stable buffered solution of an opioid antagonist at the point of absorption and for this reason applicant believes that there is no buccal opioid antagonist product in the market for life saving and other medical purposes.

In sum, a major problem with Naloxone is that it is only stable in a low pH environment e.g., a pH of 5 or less and preferably at pH 4 or lower, but that it needs to be at a higher pH (e.g. a pH greater than 5 and up to a pH of 12) in order for maximum oromucosal absorption of the drug. Therefore, there exists a need for a convenient method to administer an opioid antagonist like Naloxone that is stable over the shelf-life of the product but that can successfully deliver naloxone at high pH at the site of absorption. This invention teaches a way to administer a chemically stable aqueous liquid or semisolid gel dosage form of an antagonist through the oromucosal region (which encompasses buccal, sublingual and gingival areas). The invention shows how to achieve the contrasting requirements for stability storage pH and adequate active absorption pH for naloxone in a single dosage unit encompassing two chambers.

OBJECTS AND SUMMARY OF THE INVENTION

One object of the present invention is to provide a drug composition and delivery device for the administration of an aqueous buffered antagonist in an oral liquid or gel that is stable during the shelf life of the product.

Another object of the present invention is to provide a rapidly buffered antagonist and to rapidly increase the therapeutically effective blood levels of said antagonist.

Still another object of the present invention is to provide a portable, non-injectable oromucosal drug delivery system for opioid antagonists which can be administered in urgent medical circumstances, such as where a patient suffers from an opioid overdose but may not be located in proximity to a medical facility.

Currently there exists no method of oral or oromucosal delivery of emergency opioid antagonist. The challenge with oral delivery of opioid antagonist is with the rapid first pass metabolism of the antagonist and also that the patient in acute overdose is often unconscious. The most common treatment of overdose involves injection of the antagonist in an emergency treatment setting. Even if oral naloxone could be delivered to a patient experiencing opioid overdose, the amount of naloxone absorbed would be insufficient to reverse the overdose. Hussain et al. reports a 1% bioavailability in mice for an orally delivered Naloxone. Smith et al. also report the mean absolute bioavailability of oral Naloxone in healthy subjects at less than or equal to 2% at doses ranging from 5 mg to 120 mg. Oral administration of Naloxone for emergency treatment of opioid overdose is therefore not feasible.

As noted above, because of rapid first pass elimination of the antagonist, non-peroral administration of the antagonist is required. Parenteral administration is effective but is invasive and requires trained personnel to administer the drug to an unresponsive overdosed subject. Oromucosal absorption circumvents these problems with oral and parenteral administration because it is non-invasive and also avoids first pass metabolism of the active as it is delivered directly to the circulatory system. Further improvement of drug absorption is expected in the presence of permeation enhancer(s) or if the pH of the absorption environment is at a pH of 5 or greater as reported by Vishwas et al in the example of naltrexone. However, what Vishwas et al. fails to teach is the combination of a permeation enhancer in the presence of a buffer with a pH greater than 5. Vishwas et al. also fails to teach how to achieve the use of a buffer of pH of 5 or greater at the 'point of use/site of absorption' without loss of stability of the antagonist. See also U.S. Pat. No. 6,110,926 which, together with its contents is incorporated into this specification by reference as if fully set forth herein. In contrast, the present invention teaches how to achieve a pH greater than 5 at the point of use and site of administration, for maximal buccal absorption of the opioid antagonist while at the same time maintaining the antagonist in a lower pH environment prior to use to achieve a chemically stable product that can be stored at room temperature.

In a preferred embodiment, the composition and drug delivery system of the present invention comprises an oromucosally absorbable liquid composition for administration to a human patient of an opioid antagonist comprising one liquid containing pharmaceutical active with other suitable pharmaceutical excipients in a distinct compartment of a multi-compartment device or container comprising two or more chambers; a second liquid at pH greater than 5 containing a buffer or alkaline components with other suitable pharmaceutical excipients in a second distinct compartment of the same multi-compartment device, and a device or system which maintains separation of the first and second liquids during storage and allows for mixing of the two liquids to form an oromucosally absorbable composition of gel-like consistency at the point of use to prevent flow of the product away from administration site. For purposes of the present invention, the terms "compartment" and "chamber" are used interchangeably.

In accordance with the purposes of the present invention, as embodied and broadly described herein, the present invention includes the composition, device and method that will allow for the delivery of a stable aqueous antagonist composition to a human subjects' oromucosal region. Preferably, this is achieved by the creation of an aqueous opioid antagonist composition in the pH range of optimal stability that is housed by itself in one chamber of a multi-chambered package. In the other chamber of the package, a buffer of pH greater than 5 is housed. There exists a barrier that separates the chambers, and maintains total separation of the compositions. During use, the buffer composition and the antagonist composition are mixed together either just before being placed in the patient's mouth or within the patient's mouth, thereby delivering a buffered oromucosally absorbable mixed composition at pH greater than 5 of an antagonist at the point of absorption. The two compositions are mixed to create the final mixed composition within which the drug may no longer be storage stable, however, the mixed composition is intended to be instantly used within a few minutes of mixing and not stored for future use.

One drug in a chamber is present as a solution in water (or water plus alcohol or other co-solvents). The solution, super saturated solution, or solution with excess solid in suspension within this chamber may also have polymer/s to provide a viscous liquid or semi-solid or gel-like consistency. It may also have an acidic component or a buffer pair to bring the pH to the acidic region of pH 5 or lower to improve drug stability. It may also have colorant, permeation enhancer, an antioxidant, a dye, and/or other components as described in this specification. The other chamber contains a base or buffer pair in solution. This would typically be a higher pH buffer above pH 5 that is included for the purpose of increasing the combined solution/gel to a pH greater than 5 and maintain the pH greater than 5 or above at the site of absorption to maximize absorption. This chamber may also contain a polymer to make it a viscous liquid or gel, and it may contain dye, permeation enhancer and other pharmaceutical excipients, but an antioxidant is optional here because there is no drug in this chamber.

The two-chambered constructions disclosed herein provide some of the possible embodiments of the present invention. For example, other embodiments, as would be recognized by those of ordinary skill in the art, may contain higher multiples of compartments or chambers, and varying constructions that would achieve the objects of the present invention.

In accordance with the above objects and others, the present invention is directed in part to an oromucosally absorbable liquid composition for administration to a human patient, comprising one liquid containing a pH-sensitive pharmaceutical active together with one or more optional suitable pharmaceutical excipients in a first compartment at a pH≤5; and a second liquid at pH≥6 containing a buffer or alkaline components together with one or more optional suitable pharmaceutical excipients in a second distinct compartment; wherein the first and second compartments maintain separation of the first and second liquids during storage such that the pH-sensitive drug is maintained at a storage-stable pH and allow for mixing of the first and second liquids to form an oromucosally absorbable composition having a pH≥6 for immediate oromucosal administration to a human patient. In certain preferred embodiments, the pH-sensitive pharmaceutically active agent is an opioid antagonist (e.g., naloxone). In certain preferred embodiments, after mixing the contents of the first and second chamber, the pH of the resultant liquid is from about 6 to about 12. In certain preferred embodiments, after mixing the contents of the first and second chamber, the pH of the resultant liquid is from about 6.5 to about 9. In other preferred embodiments, after mixing the contents of the first and second chamber, the pH of the resultant liquid is from about 7.5 to about 8.5. In other preferred embodiments, after mixing the contents of the first and second chamber, the pH of the resultant liquid is 5.5, 6, 6.5, 7, 7.5, 8, 8.5, 9, 9.5, 10, 10.5, 11, 11.5 or 12. In further preferred embodiments, the pH of the liquid contained in the first compartment prior to mixing is from about 1 to about 5. In further preferred embodiments, the pH of the liquid contained in the first compartment prior to mixing is 1, 1.5, 2, 2.5, 3, 3.5, 4, 4.5, 4.6, 4.7, 4.8, 4.9, or 5. In certain preferred embodiments, the pH of the liquid contained in the first compartment prior to mixing is from about 3 to about 5.

The present invention is further directed to a method of treating a human patient in need of treatment with an opioid antagonist, comprising administering to a human patient the oromucosally absorbable liquid composition of claim 2 comprising the steps of opening the first and second compartment; causing the first and second liquids to mix; and delivering the resultant mixture to a surface within the oral cavity of the human patient. The contents of the compartments, are preferably delivered to the buccal, sublingual or gingival areas of the oral cavity.

The present invention is further directed to a method of treating a human patient in need of treatment with a pharmaceutically active agent that it is only stable in a low pH environment, comprising administering to a human patient the oromucosally absorbable liquid composition of claim 1 comprising the steps of opening the first and second compartment; causing the first and second liquids to mix; and delivering the resultant mixture to a surface within the oral cavity of the human patient. The contents of the compartments, are preferably delivered to the buccal, sublingual or gingival areas of the oral cavity.

BRIEF DESCRIPTION OF THE DRAWINGS

The accompanying drawings, which are incorporated in and form a part of the specification, illustrate the embodiments of the present invention and together with the description serve to explain the principles of the invention.

FIGS. 1a, 1b, 2a, 3a, 3b, 4a and 4b show top or bottom views of a dual-chambered package in which labeled part 1 denotes its contents as one liquid of the present invention.

FIGS. 1a, 1b, 2a, 3a, 3b, 4a and 4b show top or bottom views of a dual-chambered package in which labeled part 2 denotes its contents as a second liquid of the present invention.

FIGS. 1c, 2b, 3c, 4c and 4d show side or edge views of a dual chambered packages which contains the two liquids of the present invention.

FIGS. 1b, 1c, 2a, 2b, 3a, 3b, 3c, 4a and 4c, labeled part 3 shows the separation barrier between the first and second chambers of the present invention.

In FIGS. 5 and 6, labeled part 1 shows a view of one chamber of a dual-chambered package which contains one liquid of the present invention.

In FIGS. 5 and 6, labeled part 2 shows a view of a second chamber of dual chambered package which contains a second liquid of the present invention.

In FIGS. 5 and 6, labeled part 3 shows a view of a syringe of the present invention, which shows a separation barrier between the first and second chambers. In FIG. 5, the syringe is a double barrel syringe wherein the two barrels are conjoined and each contains the two liquids of the invention separated from one another during storage. In FIG. 6, the syringe is a single barrel syringe with a frangible barrier between the contents of the upper and lower chambers.

DETAILED DESCRIPTION OF THE INVENTION

Figure 1A:
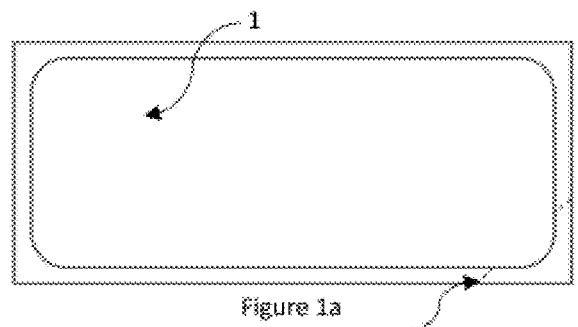
FIG. 1a, 1b, 1c, 1d, 2a, 2b, 2c, 3a, 3b, 3c and 4a, 4b, 4c and 4d show various views of four different embodiments of the device in pouch-type configurations.
Figure 1B:
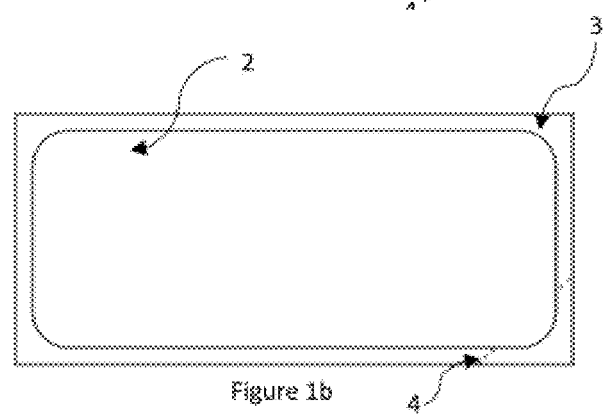
Figure 1C:
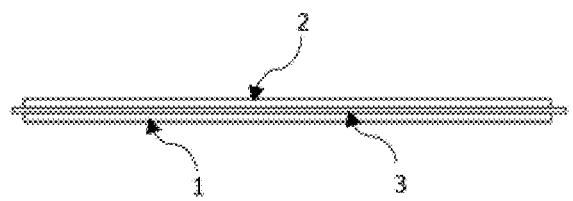
Figure 1D:
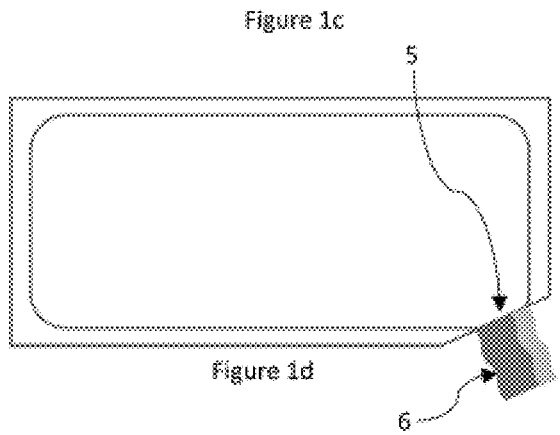
Figure 2A:
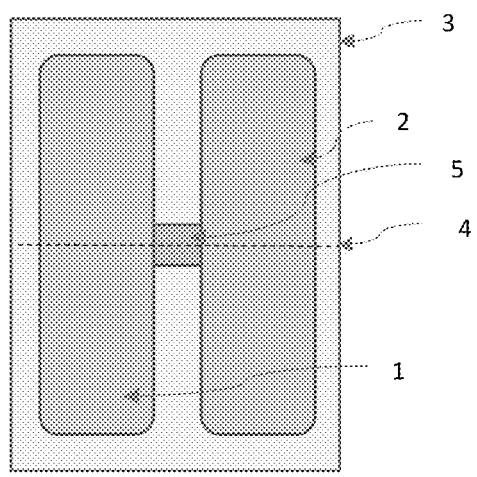
Figure 2C:
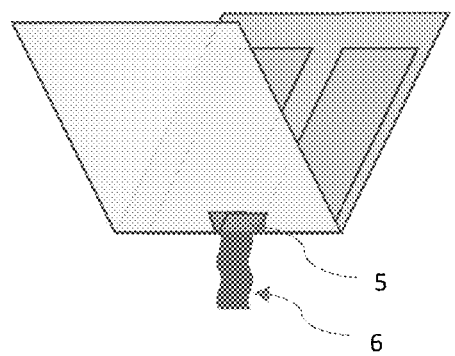
Figure 2B:
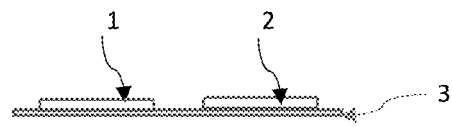
Figure 3A:
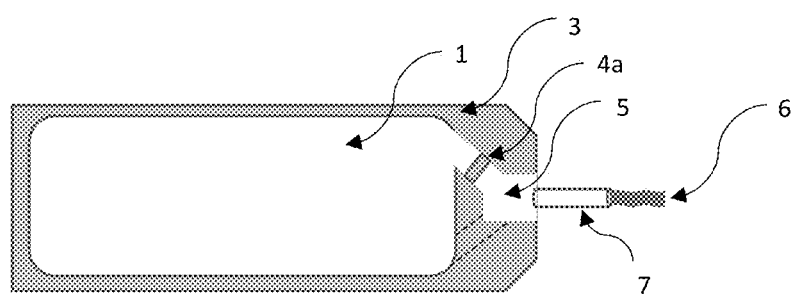
Figure 3B:
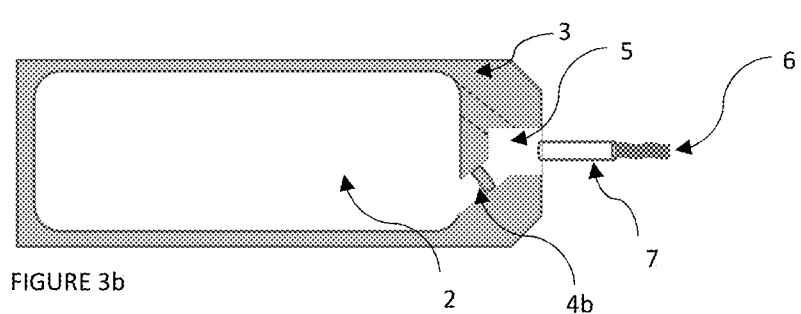

The schematic representations provided in the Figures provide description of some of the possible embodiments of the invention. During the manufacturing process the fluid containing the active drug component is deposited into one compartment labeled 1 and a buffer greater than pH 5 is deposited into a second compartment labeled part 2. Labeled part 3 represents the separation barrier between the two compartments labeled 1 and 2. In FIG. 1*a* or 1*b*, tearing along labeled part 4 causes both chambers to be opened and the compositions to exit from the pouch (labeled part 5 in FIG. 1*d*) and allow the contents (labeled part 6) to exit and be mixed at the point of use. FIGS. 2*a* and 2*c* show that the package folded along the axis part labeled 4 breaches a frangible seal labeled part 5 thereby allowing the two compositions to mix and exit the device as shown in labeled part 6. In FIGS. 3*a* and 3*b*, each of the two chambers has a frangible seal shown by labeled part 4 which may be breached by squeezing the two chambers between the fingers prior to use causing the contents of each chamber to enter a mixing zone (labeled part 5) with final exit of the mix (labeled part 6) through nozzle (labeled part 7). FIG. 4*a* shows how a first frangible seal (labeled part 4*a*) may be breached by squeezing the pouch such that contents of chamber labeled 1 and chamber labeled 2 are mixed together as shown in FIG. 4*b* prior to exiting from the pouch via nozzle labeled 7 after a second frangible seal (labeled 4*b*) is breached with further squeezing of the pouch to enable exit of the mixed composition (labeled part 6). The contents of compartment 1 and 2 are then brought together during use by various means as shown in the FIGS. 1*d*, 2*c*, 3*c* and 4*b*.

Figure 3C:
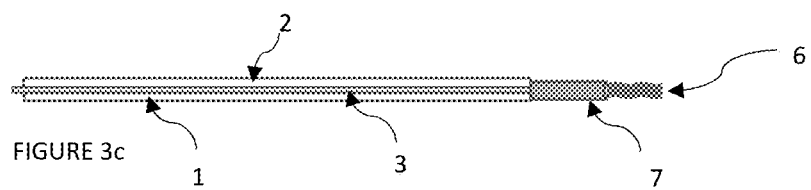
Figure 4A:
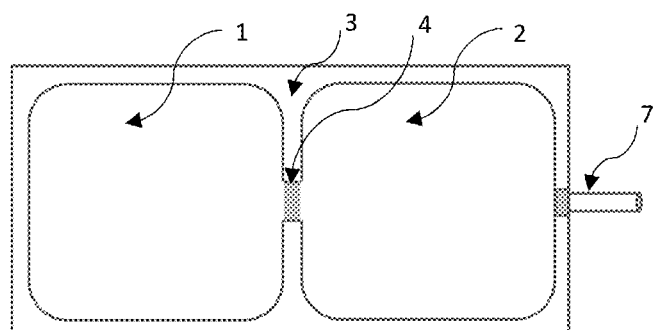
Figure 4C:
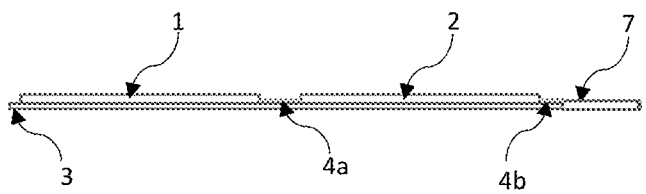
Figure 4B:
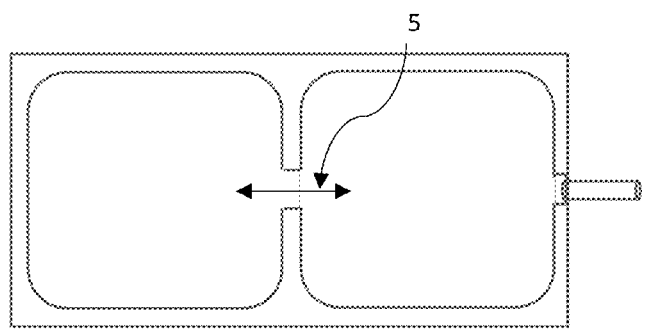
Figure 4D:

As an example, in FIGS. 3*a*, 3*b*, 3*c*, during use, the pouch is squeezed between fingers thereby breaching the frangible seals and allowing the two liquid streams to flow into a mixing zone prior to expulsion of the combined liquids from the dual compartment package. The antagonist is instantly buffered to a pH greater than 5 at the point of use, for example, in the patient's buccal, sublingual or gingival regions.

Figure 5:
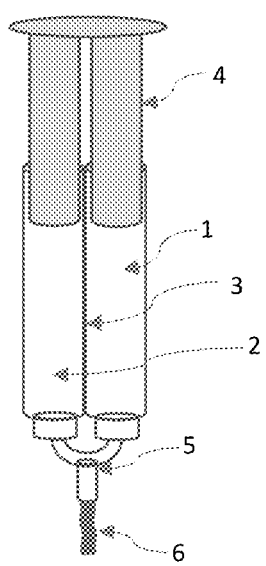
FIGS. 5 and 6 show two different emobodiments of the device in a syringe configuration.
Figure 6:
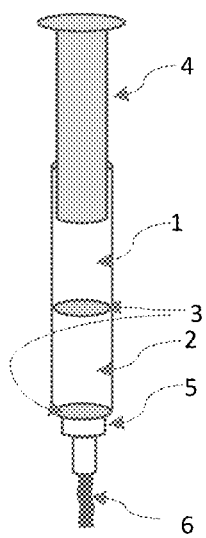

As shown in FIGS. 5 and 6, syringe designs may also be used to achieve the same objective. Similarly in FIG. 5, when plunger (labeled part 4) is depressed, the contents of the both chambers, 1 and 2, pass through a mixing zone/nozzle (labeled part 5) to exit as a combined liquid mixture (labeled part 6). In FIG. 6, when plunger (labeled part 4) is depressed, the contents of chamber 1 are forced through contents of chamber 2 and then exit through a mixing zone/nozzle (labeled part 5) to exit as a combined liquid mixture (labeled part 6). The mixing zones (labeled part 5) of FIGS. 5 and 6 may take the form of a barrel, nozzle or tip that may contain in-line mixing configurations using screw threads or other designs known in the art.

The current depiction of the pouch type embodiments in FIGS. 1*a*, 1*b*, 1*c*, 1*d*, 2*a*, 2*b*, 2*c*, 3*a*, 3*b*, 3*c* and 4*a*, 4*b*, 4*c* and 4*d* are composed of aluminum laminate foil; however, plastic, paper, metal, glass or any reasonably useful material is within the scope of the present invention. The syringe type embodiments are composed of polypropylene; however, glass, metal or any other suitable polymeric resin or other useful material is within the scope of the invention. In sum, the package or containers can be any design that can house two liquids and maintain a barrier between the two liquids and allows the two liquids to mix during use at or before the site of administration. A more liquid-like consistency is preferred for each of the individual liquid compositions so that it flows easily out and mixes readily together with each other. However, a more gel-like consistency is preferred after the liquids have combined and mixed in order to reduce flowability at the site of administration in the mouth. This would potentially allow the gel to stay in place in the oromucosal cavity and impede involuntary or inadvertent swallowing of the composition.

The antagonist composition can be of a water viscosity but preferably a viscosity of 100 cps or more is employed, and more preferably, an aqueous gel of 1000 cps and above is employed. Ideally, the viscosities of the liquids in compartments 1 and 2 should be such that efficient mixing of the liquids can be achieved.

As an example, the antagonist composition is housed in compartment 1 of FIGS. 1-6. The aqueous buffer composition of pH greater than 5 is housed in the second compartment, 2 of FIGS. 1-6, of the two-chambered package and the composition can be like water viscosity but preferably a viscosity of 2000 cps or less and more preferably an aqueous gel and can contain a water soluble polymer. The viscosity of the mixed composition (labeled part 6) of FIGS. 1-6 should be such that the liquids or gels from both compartments, 1 and 2 are readily miscible. Both the buffer and pharmaceutical active containing composition can contain a permeation enhancer.

The two chambered delivery device is arranged such that a barrier exists (FIGS. 1-6) between the two chambers in such a way that no contact between the two compositions in the two chamber occurs during storage. It is this barrier that allows for the separation of the stable aqueous antagonist solution or gel from the higher pH solution to maintain drug stability until the point of use in the oral cavity.

During use the two compositions (antagonist and buffer) in compartments 1 and 2 of FIGS. 1-6, are mixed either through turbulent mixing during expulsion from the package, or at the point of use. In this way a buffer of greater than 5 is present during the actual use of the product but does not subject the antagonist to undue storage instability by coming in direct contact with the buffer at pH greater than 5.

The antagonist is most stable at pH 5 or less; therefore suitable acidic components or buffer pairs are used to keep the antagonist at lower pH in the composition. The preferable pH for this composition is less than 5, more preferably less than 4, and most preferably 3 or less. During use of the product the antagonist's low pH buffer's capacity will be overcome by the mixing of the antagonist composition with greater than pH 5 buffer composition, which is contained in the second compartment. The final pH at the point of use will be greater than 5.

Further stability of the antagonist can be maintained during storage by the use of antioxidants and/or metal chelators and/or polyols. Either compartment can contain a pH indicator or other mixing indicators for observation and confirmation of mixing during use of the product.

Further stability of the antagonist can be maintained during storage by the use of a low pH buffer, preferably 3 or less with one or more of the following: antioxidants, metal chelators and polyols.

Both liquid compositions may contain one or more of the following: pH indicators, sweeteners, flavorings, polymers, permeation enhancers, crystallization inhibitors and other suitable pharmaceutically acceptable ingredients.

Naloxone injections are reported to be stable at pH 2.5-5. Following dilution in 5% dextrose or 0.9% sodium chloride injection to a concentration of 0.004 mg/mL (4 ug/mL), naloxone hydrochloride solutions are apparently stable for 24 hours; after 24 hours, any unused solution should be discarded. The injections also may contain methylparaben and propylparaben as preservatives. (American Society of Health System Pharmacists; AHFS Drug Information 2009. Bethesda, Md. (2009), p. 2254, hereby incorporated by reference). NARCAN® (naloxone) may be diluted for intravenous infusion in normal saline or 5% dextrose solutions. The addition of 2 mg of NARCAN® (naloxone) in 500 mL of either solution provides a concentration of 0.004 mg/mL. Mixtures should be used within 24 hours. After 24 hours, the remaining unused mixture must be discarded. The rate of administration should be titrated in accordance with the patient's response. (See, e.g., The Syringe Driver: Continuous Subcutaneous Infusions in Palliative Care By Andrew Dickman, Jennifer Schneider and also Narcan Package Insert). NARCAN® may be diluted for intravenous infusion in normal saline or 5% dextrose solutions. The addition of 2 mg of NARCAN® (naloxone) in 500 mL of either solution provides a concentration of 0.004 mg/mL. Mixtures should be used within 24 hours. After 24 hours, the remaining unused mixture must be discarded. The rate of administration should be titrated in accordance with the patient's response.

The following terms as used in the present application are illustrated as follows:

In the broadest sense, for purposes of the present invention, pharmaceutically active agent(s) which are not stable at high pH means that the pharmaceutically active agent(s) should or must be discarded after 24 hours when maintained (e.g., dissolved or dispersed) in a solution have a pH greater than 5. In certain embodiments, "not stable at high pH" means that the pharmaceutically active agent will degrade by about 15-25% over a time period of 180 days when dissolved or dispersed in a liquid having a pH greater than 6 thus making it unsuitable as a commercially viable product (e.g., that can be stored at room temperature).

For purposes of the invention, the term "stable in a low pH environment" means that the pharmaceutically active agent (e.g., opioid antagonist) in liquid 1 (pH≤5, or, e.g., pH from about 1 to ≤5) may be expected to be stable with less than 10% degradation of naloxone over 12 months.

Opioid Antagonists

The term "Opioid Antagonist" as used in connection with the present invention is meant to include one or more of the following and/or derivatives: Naloxone, Naltrexone, Nalmefene, Nalorphine, Levallorphan, Cyprodine, Naltrindole and Norbinaltorphimine.

Pharmaceutical Actives

The term pharmaceutical active or pharmaceutical active agent as used in connection with the present invention is meant to also include, in addition to opioid antagonists, any other pharmaceutical active or pharmaceutically active agent that may be systemically administered and which may benefit from preparation and administration as set forth herein. For example, the pharmaceutical active agent may be a seizure rescue medication such as anticonvulsant benzodiazepines including alprazolam, midazolam, phenazepam, nitrazepam, lorazepam, flutoprazepam, etizolam, flubromazepam, diclazepam, diazepam, cloxazolam, clonazolam, clobazam and bretazenil.

Excipients and Permeation Enhancers

Permeation enhancers that are useful to increase the absorption of the antagonist consist of the following with the more preferable permeation enhancers being the non-ionics; however, at least most of the listed compounds below all have utility as permeation enhancers.

Anionic Surfactants

Sodium octyl sulfate, Sodium decyl sulfate, Sodium dodecyl sulfate, Sodium tetradecyl sulfate, Sodium heptadecyl sulfate, Sodium eicosyl sulfate, Sodium laureth sulfate, Nicotine sulfate, Sodium taurocholic sulfate, Dimethyl sulfoxide, and Sodium tridecyl phosphate.

Zwitterionic Surfactants

ChemBetaine CAS, ChemBetaine Oleyl, ChemBetaine C, Hexadecyldimethyl ammonio propane sulfonate, Decyldimethyl ammonio propane sulfonate, Dodecyldimethyl ammonio propane sulfonate, and Myristyldimethyl ammonio propane sulfonate.

Cationic Surfactants

Benzyl pyridinium chloride, Dodecyl pyridinium chloride, Cetyl pyridinium chloride, Benzyldimethyl dodecyl ammonium chloride, Benzyldimethyl myristyl ammonium chloride, Benzyldimethyl stearyl ammonium chloride, Octyltrimethyl ammonium bromide, Decyltrimethyl ammonium bromide, Dodecyltrimethyl ammonium bromide, Myristyltrimethyl ammonium chloride, and Cetyltrimethyl ammonium bromide.

Nonionic Surfactants

Sorbitan monolaurate, Sorbitan monopalmitate, Sorbitan monostearate, Sorbitan monooleate, Polyoxyethylene sorbitan monolaurate, Polyoxyethylene sorbitan, monopalmitate, Brij 97, Brij 30, Brij 56, Brij 58, and Triton X-,100, Polyoxyethylene ethers, Polyoxyethylene esters, Polyethylene glycol esters, Sucrose esters, Sucrose ethers Fatty Acids Hexanoic acid, Octanoic acid, Decanoic acid, Undecanoic acid, Undecanoic acid, Dodecanoic acid, Tridecanoic acid, Myristic acid, Palmitic acid, Stearic acid, Oleic acid, Elaidic acid, Linoleic acid, Linolenic acid, and Cholic acid.

Fatty Esters

Methyl hexanoate, Ethyl undecanoate, Methyl laurate, Methyl tridecanoate, Methyl myristate, Isopropyl myristate, Isopropyl palmitate, Palmityl palmitate, Diethyl sebaccate, Tetracaine, Glyceryl monolaurate, Glyceryl monooleate, and Ethylpiperazine carboxylate.

Sodium Salts of Fatty Acids

N-Lauryl sarcosinate, Sodium caprylate, Sodium decanoate, Sodium palmitate, and Sodium oleate.

Fatty Amines

Octyl amine, Decyl amine, Dodecyl amine, Tetradecyl amine, Oleyl amine, and Urea.

Azone-Like Molecules

Methyl pyrrolidone, Cyclohexyl pyrrolidone, Octyl pyrrolidone, Decyl pyrrolidone, Decyl methyl pyrrolidone, Methyl piperazine, Phenyl piperazine, Octanamide, Hexadecanamide, and Caprolactam.

Others

Carveol, Pinene oxide, Limonene, Menthol, Pulegone, Carvacrol, Pinene, Menthone, Terpineol, Cineole, Fenchone, Trimethoxy propylene methyl benzene, Linalool, Geraniol, Octyl dodecanol, Phospholipids, Cyclodextrins, Chitosans.

Chelators

The term "Chelator" as used in connection with the present invention is meant to include at least one or more of the following: Ethylene Glycol Tetraacetic Acid and salts thereof (EGTA), Ethylene Diamine Tetraacetic Acid and salts thereof (EDTA), Itoic Acid, Kojic Acid, Catechol Amines, Siderophores, Hydroxamate, siderophores (ferrichrome, mycobactin, desferrioxamine, pseudobactin, aerobactin, rhodoto rulic acid, mugineic acid), histidine, cysteine, purines, pyrimidines, metalloenzymes, transport proteins, citrate, malate, histamine, adrenaline, cytochromes, spemidine. EDTA is especially useful.

Antioxidants

Antioxidants useful in connection with the present invention include primary and secondary antioxidants, including thiols, polyphenols such as Vitamin C, Tocopherols, Carotenes, Ubiquinol, Glutathione, Lipoic Acid, Eugenol, Lycopene, Resveratrol, Flavonoids, Lutein, butylated hydroxy anisole (BHA), tertiary butyl hydroquinone, and butylated hydroxy toluene (BHT) are useful. BHA, BHT are especially useful as is Vitamin C and Tocopherols.

Crystallization Inhibitors

Crystallization inhibitors useful in connection with the present invention include polyvinyl pyrrolidone (PVP), polyethylene-polypropylene glycol copolymers (Pluronics™), inulin lauryl carbamate, polyacrylate, hydroxypropyl methylcellulose (HPMC), hydroxypropyl methylcellulose acetate succinate (HPMCAS)

Polyols

The term "polyol" as used in connection with the present invention is meant to include one or more of the following: sugar alcohols, including maltitol, sorbitol, xylitol, lactitol, erythritol, hydrogenated starch hydroxysates, isomalt, glycerin, pentaerythritol, ethylene glycol, and mannitol.

Buffers

Buffer compositions useful in connection with the present invention are set forth below:

Pharmaceutically acceptable buffers of pH 5 or greater that are useful for the immediate adjustment of the antagonist at the point of use and include one or more of the following: Citric Acid/Potassium Dihydrogen Phosphate, Monosodium Phosphate/Disodium Phosphate using phosphoric acid to lower the pH or sodium hydroxide to raise the pH, Citric acid/Sodium citrate, DL-Cysteine/Sodium DL Cysteinate, Boric Acid/Sodium Hydroxide, Sodium Bicarbonate/Sodium Carbonate. Also biologically acceptable strong bases may be used in the buffer compartment, which may include Calcium hydroxide, Magnesium hydroxide, Aluminum hydroxide, Magnesium acetate, sodium hydroxide, calcium carbonate, potassium hydroxide, sodium carbonate, potassium carbonate etc.

Other acids or acidic buffers are useful for the stability protection of the antagonist and are in direct combination with the antagonist. These acids or buffers will include all systems that will create a pH less than 5, most preferably 3 or less and can include one or more of the following: Formic Acid/Sodium Formate, Hydrogen Chloride/Potassium Chloride, Hydrogen Chloride/Glycine, Hydrogen Chloride/Potassium Hydrogen Phthalate, Citric Acid/Sodium Citrate, Acetic Acid/Sodium Acetate, Citric Acid/Disodium Hydrogen Phosphate, Citric Acid/Trisodium Citrate Dihydrate, etc.

Polymers or Gel Forming Agents

The term "Water Soluble Polymer" as used in connection with the present invention and is intended to include one or more of the following: pullulan, hydroxypropyl methylcellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, Carbomers, Poylyethylene Oxides and combinations thereof. As used herein the phrase "water soluble polymer" and variants thereof refer to a polymer that is at least partially soluble in water, and desirably fully or predominantly soluble in water, or absorbs water or may form colloidal dispersions in water. The materials useful with the present invention may be water soluble at room temperature and other temperatures, such as temperatures exceeding room temperature. Moreover, the materials may be water soluble at pressures less than atmospheric pressure. Desirably, the water soluble polymers are water soluble having at least 20 percent by weight water uptake. Dosage forms of the present invention formed from such water soluble polymers are desirably sufficiently water soluble to be dissolvable upon contact with bodily fluids.

The system does not have to start as a gel and envisioned are gels that are formed in-situ when the two fluids from the chambers are brought together during use. There are certain polymers, which on their own can increase viscosity when used at low levels but when mixed with certain other excipients the viscosity changes to a semi-solid gel. Examples of such systems are carrageenan+a mono, di, trivalent cation such as calcium; gellan gum+a mono, di, or trivalent cation; sodium alginate+a cation. There are other viscous polymers that are synergistic with other polymers and will form gels such as xanthan or kappa carrageenan with locust bean gum. Also envisioned are shear thinning gels which upon mechanical shear will become quite fluid to enable complete evacuation of the fluids from each compartments but will set to a gel very quickly once the shear is removed. An example of such a system is gellan gum. Also envisioned are thermo-reversible gels, which are low viscosity at room temperature but upon entering the oral cavity at body temperature will quickly form a gel. One such system uses block copolymers and an example of such a system is Pluronic F127 alone or mixed with other polymers.

Other Useful Excipients

The present invention includes the use of certain excipients for identifying a change in pH, such as phenol red, bromothymol blue, bromo cresol purple, bromo phenol blue, litmus granules, neutral red, thymol blue, methyl orange and phenolphthalein. Also included is the use of FD & C colors and their color change to determine when fluid from chamber one mixes with fluid from chamber two. An example of such a system is yellow #5 in one chamber and blue #1 in the other chamber when brought together form green. Flavors, sweeteners and fillers are also envisioned as well as surface active agents.

EXAMPLES

The following examples demonstrate certain embodiments of the invention. Many variations of these formulations are feasible and the examples are meant for illustrative purposes only and are not meant as all encompassing. Any combination of pH values may be used based upon the stability and absorption properties of the drug being formulated and the desired pH of the individual chambers and combined gel.

Example 1

A 1 kg batch of a solution with a carbomer gelling agent is prepared as follows. Percentages are w/w % of the final 1 kg batch.

Purified water (96.45%; 964.54 g) is added to a 0.5 gallon kettle equipped with a mixing apparatus (counter-rotating mixer or propeller mixer). The water is heated to about 40° C. and is stirred. The temperature is maintained, the stirring speed is increased to about 1200 RPM, and Carbomer 940 (0.546%; 5.46 g) is slowly added until a homogeneous mixture is formed. The mixture is stirred for an additional 45 minutes at about 40° C. and propylene glycol (3%; 30 g; heated to about 40° C.) is added to the mixture and stirred for 15 minutes. Water is added back to the mixture to obtain 1000 grams and mixing is continued at about 12 RPM, avoiding aeration. The temperature is maintained for about 15-30 minutes to form Liquid Mixture A. Separately, two buffers are prepared. The first buffer is prepared at a target pH of 5.8 and the second buffer is prepared at a target pH of 8. The first buffer of pH 5.8 contains 0.207 ml of 2 mol/1 of Acetic Acid and 2.294 ml of a 2 mol/1 of NaAcetate. The second buffer of pH 8 contains 0.204 ml of a 2 mol/1 of sodium dihydrogen phosphate and 2.296 ml of a 2 mol/1 of disodium hydrogen phosphate. The buffers are designated as Buffer 5.8 and Buffer 8.

Five hundred grams of Liquid Mixture A is weighed into a separate stirring vessel and the 5.8 buffer is added with slow mixing. The mixture is stirred under 28 in. Hg. vacuum for 12 minutes and is designated Liquid Mixture B.

Five hundred grams of Liquid Mixture A is weighed into a separate stirring vessel and buffer 8 is added with slow mixing. The mixture is stirred under 28 in. Hg. vacuum for 12 minutes and is designated Liquid Mixture C.

In a separate mix procedure a repeat of Liquid Mixture A is performed into which 12.2 grams of Naloxone HCl is added. The pH is adjusted to 3 using citric acid and sodium citrate. EDTA (1% wt/wt %) is added to the solution. This will equate to 10 mg of Naloxone base per gram of gel and is designated Liquid Mixture D.

One gram of Liquid Mixture D is added to compartment 1 of FIGS. 1-6 of the two sided pouch or syringe and one gram of Liquid Mixture B is added to the other compartment 2 of FIGS. 1-6 of the pouch or syringe. The gels are combined prior to use and extruded, from the package (labeled part 6 in FIGS. 1-6) and the sample is designated Combined Gel Mixture 1 at 5.8 pH.

One gram of Liquid Mixture D is added to the first compartment 1 of FIGS. 1-6 of the two side pouch or syringe and one gram of Liquid Mixture C is added to the other compartment 2 of FIGS. 1-6 of the pouch or syringe. The gels are combined prior to use and extruded, from the package (labeled part 6 in FIGS. 1-6) and the sample is designated Combined Gel Mixture 2 at pH 8.

Example 2

HPMC E15+Polyethylene Oxide N80+Maltitol at a ratio of 2:1:1 are combined with 1% (wt. %) Citric Acid and 1% (wt. %) Edetate Disodium and 1% (wt. %) Etocas 35 and 0.5% (wt. %) Glycerol Monooleate. The combination (20 grams) is combined with water (80 grams) and stirred for 3 hour using a gate impeller. During the last hour of mixing, vacuum was set at 27-28 inches of Hg to deaerate the mixture. To 97.58 grams of this mixture is added 2.42 grams of naloxone HCl dihydrate to obtain 20 mg of Naloxone base per gram of polymer gel solution. This mixture is designated as Liquid Mixture A2.

Another polymer mixture of 20 grams is made using HPMC E15+PEO N80+Maltitol+Propylene Glycol Alginate in 2:1:1:1 ratio. The psame commentolymer blend is added to 75 grams of water. To this mixture 4 grams of a buffer pH 8 is added, which contains 0.204 ml of a 2 mol/1 of sodium dihydrogen phosphate and 2.296 ml of a 2 mol/1 of disodium hydrogen phosphate, and 1 gram of Glycerol Monooleate are added to the polymer mixture and the combination is mixed 3 hours using a gate impeller. During the last hour, vacuum is applied at 27 to 28 in Hg. to de-aerate the polymer mixture. This mixture is designated as Liquid Mixture B2.

One gram of Liquid Mixture A2 (20 mg of Naloxone base) is added to compartment 1 of FIGS. 1-6, and one gram of Liquid Mixture B2 is added to the other compartment 2 of FIGS. 1-6. The gels are combined prior to use and extruded, from the package (labeled part 6 in FIGS. 1-6) and the sample is designated Combined Gel Mixture 3 at pH 8.

Example 3

The following composition was tested in a dog study. The formulation administered to dogs was composed of two component gels, Liquid Mixture A and Liquid Mixture B. Table 1 shows the composition of Liquid Mixture A. Liquid Mixture A was made in the following manner.

Ingredients 1, 2, 3, 4, 5 and 7 were dry blended together. Ingredient 6 and 8 were added to a 250 ml beaker and mixed for 20 minutes using a magnetic stirrer. Ingredients 1, 2, 3, 4, 5 and 7 were added slowly to the beaker with continued stirring. Once all the ingredients were wetted the mixture was sealed and placed in a refrigerator (2-8° C.) for 24 hrs. After 24 hours the solution/suspension was removed and allowed to reach room temperature. A drop placed on the skin gelled upon contact indicating a proper thermal gelation at body temperature. The sample was designated as Liquid Mixture A pH 3.0. A quantity of naloxone slightly in excess of the solubility limit of naloxone at room temperature was added to the Liquid Mixture A pH 3.0. The formulation sample was used in beagle dog opioid overdose reversibility study.

TABLE 1 pH 3.2 Naloxone Liquid Mixture A

| Ingredient Number | Name | Amount (grams) |
|---|---|---|
| 1 | Pluronic F127 | 16.22 |
| 2 | Sorbitol | 2.0 |
| 3 | Citric Acid | 0.37 |
| 4 | Na Citrate | 0.16 |
| 5 | EDTA | 0.04 |
| 6 | Brij 58 | 1.0 |
| 7 | Naloxone HCl 2H$_2$O | 6.34 |
| 8 | Water | 73.87 |
| TOTAL | — | 100.0 |

Liquid Mixture B composition is shown in table 2 below. Liquid Mixture B was made in the following manner.

Ingredient 4 was added to a 250 ml beaker and stirred with a magnetic stirrer. Ingredients 1, 2 and 3 were dry blended and added slowly to the beaker and stirred with the magnetic stirrer until all ingredients were wetted. The mixture was placed in a refrigerator (2-8° C.) for 24 hrs. After 24 hours the solution was brought to room temperature and a drop placed on the skin gelled upon contact indicating a proper thermal gelation at body temperature. The sample was designated Liquid Mixture pH 10. This Liquid Mixture B was used in dog opioid overdose reversibility study.

TABLE 2 pH 10 Liquid Mixture B

| Ingredient | Ingredient | Weight |
|---|---|---|
| 1 | NaOH | 0.6 |
| 2 | NaHCO3 | 3.0 |
| 3 | Pluronic | 17.3 |
| 4 | Water | 79.05 |
|  |  | 100 |

A 1:1.6 ratio of Liquid Mixture A pH 3: Liquid Mixture B pH 10 was used in the dog study. When added together, the Combined Gel Mixture had a pH of 8.7. It was found in the laboratory that when this combined gel was added to 1 g of human saliva at pH 6.23, a final pH of 8.26 was achieved. This demonstrated that the pH at site of absorption is high enough to insure proper absorption of the Naloxone. 1 g of low pH gel contains 63.4 mg of Naloxone HCl dihydrate and will require 2.6 grams of the Combined Gel Mixture in the 1:1.6 ratio of Liquid Mixture A and Liquid Mixture B.

Animal Opioid Overdose Reversibility Study

Two Beagle dogs approximately 10 months old, weighing 11.3 kg and 10.5 kg were used in this study. The animals were fasted overnight, weighed, and observed for clinical observations, including baseline heart and respiration rates. Fentanyl citrate (concentration—0.05 mg/mL) via slow bolus intravenous injection was used to achieve sedation.

Once sedation was reached, the components of the test article (Liquid Mixture-A and Liquid Mixture B) were combined using a dual syringe system to form a Combined Gel Mixture. Liquid Mixture A was placed in one syringe and Liquid Mixture B was placed in the second syringe. Mixture of the gel was achieved by plunging the syringes through a mixing chamber. The Combined Gel Mixture was administered within 1 minute of combination to both animals.

Results

A total of 6 mL of fentanyl was administered to both animals over three minutes to achieve sedation. Sedation was characterized by onset of CNS depression, reluctance to stand, decreased responses to stimuli, absence of toe-pinch reflex, eyes positioned ventro-medially. Mucus membranes were cyanotic and the respiratory rate was 16/min to 18/min for both animals. The first sedated animal received 2.6 g of Combined Gel Mixture (1 g of Liquid Mixture A+1.6 gram of Liquid Mixture B) and completely recovered, was able to stand and was mentally alert within seven minutes after application of the combined gel mixture. The respiratory rate had increased from 16/minute before application of the gel to 24/minute after the application of the gel.

Figure 7:
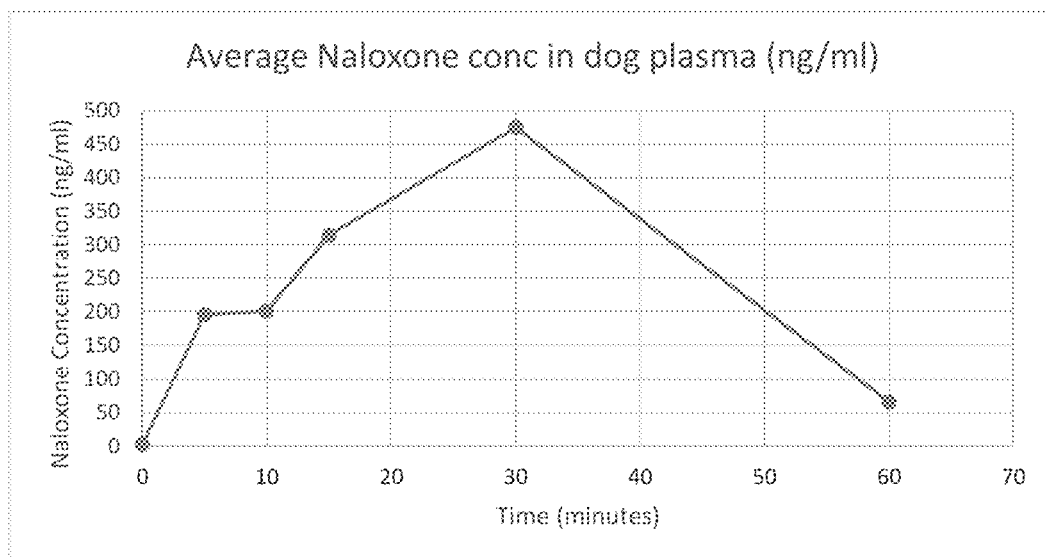
FIG. 7 is a graph of Naloxone plasma levels for test animal.

The second sedated animal received 3.9 g of Combined Gel Mixture (1.5 g of Liquid Mixture A and 2.4 g of Liquid Mixture B) and completely recovered, was able to stand and was mentally alert within 5 minutes after application of the Combined Gel Mixture. The respiratory rate increased from 18/min. before application of the gel mixture to 24/min. after the application of the gel. Blood samples were drawn from this dog at 5, 10, 15, 20, 30 and 60 minutes. Plasma concentration of naloxone for the second animal is shown in FIG. 7.

CONCLUSION

Initial vital signs and doses of fentanyl required to reach sedation were nearly identical for both study animals: The Combined Gel Mixture (Liquid Mixture A+Liquid Mixture B) when given at a total dose of 5.5 mg/kg resulted in a recovery from sedation which required seven minutes whereas increasing the dose to 8.9 mg/kg resulted in a recovery from sedation requiring only five minutes. Either dose was sufficient for compete recovery from sedation for both animals within 10 minutes. As seen from the blood plasma levels shown in FIG. 7 naloxone was rapidly absorbed from the oromucosal cavity. At about the time taken for the animal to revive (5 minutes), the concentration of naloxone was approximately 200 ng/ml, however the plasma naloxone concentration continued to rise and was measured at almost 2.5 times the level seen at 5 minutes. This indicated that the amount of buccal gel required to revive the animal may be considerably less than the 8.9 mg/kg that had been administered. Compared to parenteral administration, only a fraction of the drug may be expected to reach the systemic circulation when administered via the oromucosal route. Since a relatively large surface area is available in the oromucosal cavity, a range of therapeutic levels of drug can be readily achieved in human subjects depending upon the dose of gel administered.

The foregoing description of the present invention has been presented for purposes of illustration and description and is not intended to be exhaustive or to limit the invention to the precise form disclosed, and obviously many modifications and variations are possible in light of the above teaching.

The invention claimed is:

1. A kit for administering an oromucosally absorbable gel composition to a human patient, comprising a first compartment comprising a first liquid containing a pH-sensitive pharmaceutical active agent comprising an opioid antagonist together with one or more optional suitable pharmaceutical excipients at a pH≤5; and a second compartment comprising a second liquid at pH≥6 containing a buffer or alkaline components together with one or more optional suitable pharmaceutical excipients, at least one of the first and second liquids contains a crystallization inhibitor; wherein the first and second compartments maintain separation of the first and second liquids during storage such that the pH-sensitive pharmaceutical active agent is maintained at a storage-stable pH and allow for mixing of the first and second liquids to form an oromucosally absorbable gel composition having a pH for immediate oromucosal administration to a human patient.

2. The kit for administering an oromucosally absorbable gel composition of claim 1, wherein the opioid antagonist is naloxone.

3. The kit for administering an oromucosally absorbable gel composition of claim 2, wherein after mixing the contents of the first and second compartments, the pH of the resultant gel is from 6 to about 12.

4. The kit for administering an oromucosally absorbable gel composition of claim 2, wherein after mixing the contents of the first and second compartments, the pH of the resultant gel is from about 6.5 to about 9.5.

5. The kit for administering an oromucosally absorbable gel composition of claim 2, wherein after mixing the contents of the first and second compartments, the pH of the resultant gel is from about 7 to about 9.

6. The kit for administering an oromucosally absorbable yel composition of claim 2, wherein the pH of the liquid contained in the first compartment prior to mixing is from about 1 to about 5.

7. The kit for administering an oromucosally absorbable yel composition of claim 1, wherein the pH of the liquid contained in the first compartment prior to mixing is from about 3 to about 5.

8. The kit for administering an oromucosally absorbable yel composition of claim 3, wherein the pH of the liquid contained in the first compartment prior to mixing is from about 3 to about 5.

9. The kit for administering an oromucosally absorbable gel composition of claim 1, wherein the one or more optional suitable pharmaceutical excipients in either the first compartment or the second compartment is selected from the group consisting of a permeation enhancer, a chelator, an antioxidant, a gel forming agent, and combinations of any of the foregoing.

10. The kit for administering an oromucosally absorbable gel composition of claim 1, wherein the first and second compartments are syringe chambers axially conjoined together.

11. The kit for administering an oromucosally absorbable gel composition of claim 10, further comprising a mixing tip for mixing the contents of the first and second compartments.

12. The kit for administering an oromucosally absorbable yel composition of claim 11, wherein the first and second compartments are in a single barrel and are separated by a frangible barrier.

13. The kit for administering an oromucosally absorbable yel composition of claim 1, wherein the first and second compartments are contained within a single pouch, the first and second compartments being separated by a barrier.

14. The kit for administering an oromucosally absorbable gel composition of claim 13, further comprising a mixing zone for mixing the contents of the first and second compartments.

15. The kit for administering an oromucosally absorbable gel composition of claim 14, wherein the liquids contained in the first and second compartments are sealed within the compartments by a frangible seal separating the compartments from the mixing zone.

16. A kit for administering a stable, oromucosally absorbable, pharmaceutical active agent gel composition to a human subject, comprising a first compartment comprising a pharmaceutically active agent solution comprising an opioid antagonist maintained at a pH range suitable for maintaining the stability of the opioid antagonist, and a second compartment comprising a pH adjusting liquid having a pH at which the pharmaceutically active agent solution is not stable, wherein the first and second compartments maintain the pharmaceutically active agent solution separate from the pH adjusting liquid until the pharmaceutical active agent composition is to be administered to a human, at least one of the pharmaceutically active agent solution and the pH adjusting liquid contains a crystallization inhibitor, and the first and second compartments allow the pharmaceutically active agent solution and the pH adjusting liquid to be combined to form an oromucosally absorbable gel composition prior to administration to the human.

17. The kit for administering an oromucosally absorbable gel composition of claim 1, wherein the first compartment contains the opioid antagonist in solution with an acid, and the second compartment contains a base and a conjugate acid.

18. The kit for administering an oromucosally absorbable gel composition of claim 1, wherein the oromucosally absorbable gel composition is thermo-reversible.

19. The kit for administering an oromucosally absorbable gel composition of claim 1, wherein at least one of the first and second liquids is shear-thinning.

20. The kit for administering an oromucosally absorbable yel composition of claim 1, wherein the oromucosally absorbable gel composition is a super saturated solution.

21. The kit for administering an oromucosally absorbable yel composition of claim 1, wherein one of the first and second liquids contains a polymer that when mixed with a cation excipient changes the viscosity to form a semi-solid gel, and another of the first and second liquids contains the cation excipient.

22. The kit for administering an oromucosally absorbable gel composition of claim 1, wherein one of the first and second liquids contains a polymer that when mixed with a synergistic polymer changes the viscosity to form a semi-solid gel, and another of the first and second liquids contains the synergistic polymer.

23. The kit for administering an oromucosally absorbable gel composition of claim 1, wherein at least one of the first and second liquids contains a mixing indicator for observation and confirmation of mixing during use of the product.

24. The kit for administering an oromucosally absorbable gel composition of claim 23, wherein the mixing indicator is a pH indicator.

25. The kit for administering an oromucosally absorbable yel composition of claim 1, wherein the opioid antagonist is naltrexone.

26. The kit for administering an oromucosally absorbable yel composition of claim 1, wherein the first liquid containing a pH-sensitive pharmaceutical active agent comprising an opioid antagonist comprises naloxone and naltrexone.

27. The kit for administering a stable, oromucosally absorbable, pharmaceutical active agent gel composition of claim 16, wherein the opioid antagonist is naloxone.

28. The kit for administering an oromucosally absorbable gel composition of claim 1, wherein the opioid antagonist is naltrexone.

29. The kit for administering an oromucosally absorbable gel composition of claim 1, wherein the pH-sensitive pharmaceutical active agent comprising an opioid antagonist comprises naloxone and naltrexone.

* * * * *